United States Patent
Kiesewetter et al.

(10) Patent No.: US 7,208,281 B2
(45) Date of Patent: Apr. 24, 2007

(54) LIGANDS USED FOR DETECTING PRIONS

(76) Inventors: Holger Kiesewetter, Am Grünen Zipfel 1, 13465 Berlin (DE); Abdulgabar Salama, Lotosweg 6, 13467 Berlin (DE)

( * ) Notice: Subject to any disclaimer, the term of this patent is extended or adjusted under 35 U.S.C. 154(b) by 16 days.

(21) Appl. No.: 10/467,612

(22) PCT Filed: Feb. 12, 2002

(86) PCT No.: PCT/EP02/01451

§ 371 (c)(1),
(2), (4) Date: Dec. 8, 2003

(87) PCT Pub. No.: WO02/065133

PCT Pub. Date: Aug. 22, 2002

(65) Prior Publication Data

US 2004/0096902 A1    May 20, 2004

(30) Foreign Application Priority Data

Feb. 13, 2001  (DE) ................................ 101 07 083

(51) Int. Cl.
| | | |
|---|---|---|
| *G01N 33/53* | (2006.01) | |
| *G01N 33/552* | (2006.01) | |
| *G01N 33/533* | (2006.01) | |
| *G01N 33/546* | (2006.01) | |
| *C12Q 1/37* | (2006.01) | |
| *C07K 16/00* | (2006.01) | |

(52) U.S. Cl. .......................... 435/7.1; 435/7.5; 435/23; 436/527; 436/533; 436/546; 530/387.1; 530/391.1

(58) Field of Classification Search ................. 435/7.1, 435/7.5, 23; 530/391.1, 387.1; 436/527, 436/546, 533

See application file for complete search history.

(56) References Cited

U.S. PATENT DOCUMENTS

2001/0005578 A1* 6/2001 Prusiner et al. ................ 435/2
2001/0010918 A1* 8/2001 O'Connor .................... 435/7.1
2005/0208608 A1* 9/2005 Raven et al. ................... 435/8

FOREIGN PATENT DOCUMENTS

DE      197 30 132 A1      2/1999
WO      WO 00/29850        5/2000

OTHER PUBLICATIONS

"Binding of the Protease-Sensitive Form of Prion Protein PrP to Sulfated Glycosaminoglycan and Congo Red", Caughey et al., Journal of Virology, vol. 68, No. 4, Apr. 1994, pp. 2135-2141.
"Characterization and Polyanion-binding Properties of Purified Recombinant Prior Protein", Brimacombe et al., Biochem. J., 1999, pp. 605-613.
International Search Report in PCT/EP02/01451 dated Oct. 11, 2002.
International Preliminary Examination Report in PCT/EP02/01451 dated Jan. 9, 2003.

* cited by examiner

*Primary Examiner*—Long V. Le
*Assistant Examiner*—Shafiqul Haq
(74) *Attorney, Agent, or Firm*—Marshall, Gerstein & Borun LLP

(57) ABSTRACT

The invention relates to the use of specific ligand carriers for detecting prions, and to substances that are capable of binding to prions and that are subsequently used to detect prions.

16 Claims, No Drawings

LIGANDS USED FOR DETECTING PRIONS

This is the U.S. national phase of International Application No. PCT/EP02/01451 filed Feb. 12, 2002, the entire disclosure of which is incorporated herein by reference.

The present invention relates to the use of ligands for detecting prions, in particular in connect with a high speed bovine spongiform encephalopathy (BSE) test. Moreover, substances are disclosed which are suitable for binding and the subsequent determination of prions.

Prions are normal cellular proteins (PrPc) which can be detected above all on the surface of neurons. By conversion of the normal cellular protein into its abnormal isoform (PrPsc), a pathogenic form with new properties is formed. In contrast to the normal form, the form thus obtained is not water-soluble and cannot be degraded by proteases. According to the so-called "protein only" hypothesis, the simultaneous occurrence of pathological and normal prions results in the normal molecule changing its conformation and adopting the pathological form. This process leads to the accumulation of these proteins in the brain and finally to encephalopathies which include the Traber disease (scrapie) in sheep, the bovine spongiform encephalopathy (BSE) in cattle and the Creutzfeldt-Jakob disease (CJD) in man.

Glycosaminoglycans (GAGS) are linear heteropolysaccharides which are anchored to the cell surfaces and play a major role in cell adhesion and migration. The intracellular insertion of prions via these molecules is also possible.

Pentosan (poly-b-xylose-2,3-disulphonate; pentosan polysulphonate) is a polysulphonated polyglycoside (molecular weight 4,000 to 12,000 Dalton). This molecule seems to inhibit the accumulation of prions. It has been shown that, in comparison with other sulphonated GAGS such has heparin, heparan sulphate and chondroitin sulphate, this substance inhibits the production of prions most strongly. This inhibition may be attributable to a direct linkage with the prions [B. Caughey and G. Raymond, Journal of Virology, February 1993, p. 643–650; B. Caughey et al, Journal of Virology, April 1994, p. 2135–2141; D. Sawitzky, Med. Microbiol Immunol. (1996) 184: 155–161; R. Gabizon et al, Journal of Cellular Physiology 157: 319–325 (1993); Show-Ling Shyng et al., Journal of Biological Chemistry, 1995 by the American Society for Biochemistry and Molecular Biology, Inc., C. Farquhar et al, The Lancet, Vol. 353, Jan. 9, 1999].

PrP-specific monoclonal and polyclonal antibodies have already been produced which recognise both variants PrPc and PrPsc. By means of the monoclonal antibodies available, the two variants can be differentiated indirectly and a disease detected in this way.

This has so far been done by mixing the samples to be examined with proteinase K which destroys only PrPc but not PrPsc. By means of electrophoresis, both proteins are separated and the pathological form is detected with antibodies. Although the sensitivity and specificity of this test is high, not all cases of BSE can be detected since a positive result in these tests depends on the total quantity of the prions used for the investigation. However, a sufficiently high overall amount is present in the brain tissue as a rule only during the final stage of the disease so that, so far, it has been possible to carry out the corresponding investigations in a standard manner only on tissue from dead beings (R. Meyer, Dt. Ärzteblatt 97, Vol. 49, Aug, 12, 2000, page A-3314). Moreover, these tests based on electrophoresis are time-consuming and expensive.

Recently, it has been possible to track down the pathogens also in the blood of sheep and moose by means of organic solvents and a special type of chromatography and to detect them by means of a Western blot test [M. Schmerr et al., Journal of Chromatography A, 853 (1999) 207214]. However, such a test is extremely time-consuming and expensive and hardly feasible in practice as routine test.

Adriano Aguzzi et al. recently described PrPsc as binding specifically to plasminogen [M. B. Fischer et al, NATURE, Vol. 408, 23. November 2000]. A test based on this binding was not presented.

It has thus not been possible so far to find specific laboratory markers for these diseases and, as a rule, the diagnosis is possible only after the death of the patient or after the animal has been killed [S. B. Prusiner, PNAS USA, Vol. 95, pp. 13363–13383, November 1998; A. L. Horwich and S. Weissman, Cell, Vol. 89, 499–510, May 1997].

In DE 197 30 132 A1 and WO 00/29850, in vitro methods for the detection of BSE pathogens in a specimen are described; however, in contrast to the method according to the invention, the detection is carried out directly by means of immobilised antibodies. The use of glycosaminoglycan is not described.

Until the present invention was made, it had not been possible to implement any process commercially by means of which any BSE disease might have been detectable in living organisms. However, it would be precisely this which—in view of the present incurability of this disease and the proven transferability of the disease from infected animals (e.g. cattle) in which the disease need not yet have broken out, however, to man via the food consumed—would be of paramount importance for the comprehensive prophylaxis and for the successful elimination of the disease. In this connection, the economic losses caused by this disease amounting to billions also deserve to be mentioned.

In spite of the extremely high need for a BSE test overcoming the above-mentioned disadvantages, which necessarily arises from the details stated above, it has not been possible, up until the present invention, to provide such a test.

In view of the above-mentioned state of the art, the present invention is consequently based on the task of providing a method by means of which BSE pathogens (PrPsc) can be specifically detected. This method should be easy and rapid to handle and safe and cost-effective to execute and permit an extremely sensitive detection. Moreover, it should be possible to carry out this method in vitro on samples with low PrPsc concentrations which can be obtained from living organisms, for example.

This task and others not explicitly mentioned which nevertheless can be directly derived or deduced from the contexts discussed above are achieved by the inventive method.

By treating, in an in vitro process, (i) a sample with proteinase K (ii) bringing the sample thus treated into contact with a binding principle which is bound to a solid carrier (iii) separating the binding principle bound to the solid carrier from the sample and (iv) detecting the BSE pathogen (PrPsc) which, if necessary, is bound to the binding principle and originates from the sample, whereby (v) the binding principle (ii) is selected from the group consisting of: a glycosaminoglycan, fibronectin or lipoprotein A, it is possible to make a process available in a not directly foreseeable manner for detecting BSE pathogens in a sample, which process allows this detection to take place in a simple manner. In this connection, this process exhibits the above-mentioned advantages compared with the state of the art.

In particular, it is
simple and rapid to handle and
safe and cost-effective to execute and it can
be carried out on samples originating from living organisms such as blood samples, tissue samples or body fluids such as urine, milk, liquor or saliva or on soil or plant specimens According to the invention, BSE pathogens are detected. This should be understood to mean the pathological form of the prion protein (PrPsc).

For the degradation of the non-pathological prion protein (PrPc), proteinase K is added to the sample. It is known from the state of the art that proteinase K hydrolytically splits the non-pathological form but the pathological form of the prion protein only to a small extent. In view of the present invention, however, it is clear to the persons skilled in the art that other proteases which satisfy the above-mentioned purpose can also be used according to the invention without deviating from the scope of the present invention. The hydrolytic splitting processes using proteinase K are well known to the persons skilled in the art. In particular, a series of operating procedures are contained in laboratory handbooks in which the buffer systems suitable for use, the incubation periods to be applied and other reaction conditions to be satisfied are described in detail.

The hydrolytic degradation of the non-pathological prion protein with proteinase K is described by M. Schmerr et al, in Journal of Chromatography A, 853 (1999) 207–214, for example.

It is, for example, possible to degrade the PrPc by subjecting a sample to a 30 minute degradation by proteinase K in a 250 μg/ml proteinase K solution in a commonly used Tris/EDTA buffer, pH 7.4, 37° C.

The prion proteins which are not hydrolytically split and which, according to the invention, represent the pathological PrPsc form are removed from the sample by means of a binding principle. This binding principle consists preferably of a glycosaminoglycan, particularly preferably pentosan polyphosphate. Other preferred glycosaminoglycans which can be used according to the invention are: heparan sulphate, heparin, hyaluronic acid, chondroitin sulphate, dermatan sulphate, keraton sulphate or Congo Red. Similarly preferably usable according to the invention is an artificially produced sulphonated glycosaminoglycan. Fibronectin can also be preferably used as binding principle. Lipoprotein A can also be preferably used as binding principle.

According to the invention, this binding principle is bound to a solid carrier.

Preferably, all solid carriers which are known to the persons skilled in the art in the field of affinity chromatography can be considered for use as solid carrier. Particularly preferably, so-called beads are used according to the invention, i.e. usually spherical micro-carriers of different materials.

Other solid carriers which can preferably be used according to the invention are those column materials which have found widespread use in affinity chromatography.

Microtiter plates coated with the binding principle described above are also preferably used according to the invention.

Nanobeads containing europium (Eu), from Seradyn, Indianapolis, USA, are particularly preferred. These particles are "absorbed" with europium chelates in such a way that the surface remains free for coupling reactions and the europium chelates do not escape. Europium chelate: tris (naphthyl trifluorobutanedione) Eu. When these particles are stimulated with UV light (333 nm maximum), they emit light radiation at 613 nm with a duration of approximately 0.5 milliseconds which is 10,000 to 100,000 times longer than the emission period of most flurophores. This extremely long emission period and the large Stokes displacement (difference between emission and excitation wavelength) permits their use in the tests based on time-delayed fluorescence. Each particle contains >30,000 europium atoms in tris-naphthyl trifluorobutanedione (a diketone). For the 100 nm particles, the so-called quantum yield is equivalent to approximately 3,000 molecules of fluorescein (one of the most widely used fluorophores). Phycobiliprotein (probably the most strongly fluorescent compound known), in comparison, has a quantum yield corresponding to that of approximately 30 fluorescein molecules. Since a 100 nm particle has a diameter approximately 10 times bigger than the phycobiliprotein and a 1000 times larger volume mass ratio, these beads have a fluorescence which, on a molar basis, is 100 times higher than that of phycobiliprotein.

The nanoparticles are first irradiated (the so-called excitation wavelength for europium is 340 nm) and, after a delay of 400 μs (in this case), the signals are measured for a length of 400 μs. As a result of this delay, registering non-specific signals of short duration from the matrix is avoided. The results are recorded in RFU (relative fluorescence units). The measuring operation takes place automatically by means of a standardised fluorimeter which can be used to measure time delayed fluorescence.

By means of the test system according to the invention, investigations are successfully carried out on samples originating from living organisms, such as blood samples, tissue samples or body fluids such as urine, milk, liquor or saliva for the presence of BSE pathogens (PrPsc; pathological form of the prion protein).

It is also possible to carry out investigations into soil or plant specimens.

Particularly preferably, thrombic starting material subjected to lysis is used as sample. For this purpose, a blood sample is caused to clot and the thrombic material thus formed is separated off. The thrombic material is degraded by hydrolysis with a proteinase and the resulting sample is used directly in the test.

The BSE pathogen bound to the binding principle is preferably detected by specific antibody tests. These tests and the method of detection are also well known to the persons skilled in the art. ELISA and RIA methods as well as agglutination tests and flow cytometry can be mentioned as examples.

In principle, all processes can be applied which permit detection via a specific initial antibody, if necessary by using a second antibody specific for the first antibody. Methods which include a reinforcing system such as an enzyme coupled to a first or second antibody can be used particularly preferably according to the invention.

Specific antibodies have already been described and can be purchased from Prionics AG, University of Zurich, Switzerland.

A system particularly preferred according to the invention for the detection of the PrPsc bound to the binding principle comprises antibodies covalently bound to nanoparticles with a diameter of 10–100 nm. The nanoparticles contain europium. By means of time-delayed fluorescence, these particles and consequently indirectly the antibodies or the binding of the antibodies to PrPsc or to the first antibody can be detected highly sensitively.

Moreover, it is preferred for the antibodies of the above-mentioned paragraph to be bound to the nanobead not covalently but via the biotin/streptavidin system which is well known to the person skilled in the art, the antibody being preferably present in the biotinylated state.

A further preferred practical example of the present invention involves the carrier being present in the labelled state for the detection, in particular in the form of a Eu labelling (Eu nanobeads) and, following depletion from the sample by binding to a second binding principle, in particular a specific anti-PrPsc antibody, detecting the corresponding labelling by the corresponding detection, in particular time-delayed fluorescence.

A characteristic feature of the present invention is that the individual aspects of the detection process according to the invention are known to the persons skilled in the art. However, it was impossible to foresee in any way that a combination of these individual steps would lead to a method which, in such a highly surprising and favourable manner, provides a simple solution to such intensive needs of the persons skilled in the art.

The following examples provide a more detailed explanation of the invention. However, they should not be understood to be limiting in any way.

EXAMPLE 1

Binding of Pentosan to Microcarriers.

Toyopearl HW55 (commercially available cross-linked polyacrylate gel from Toyo Soda Manufacturing Co. Ltd. with a particle size of 50–100 μm) was used as the carrier.

6 ml of a saturated aqueous NaOH solution and 15 ml epichlorohydrin were introduced into 10 ml of the gel and the reaction mixture was incubated for two hours with stirring at 50° C. The gel was washed in sequence with alcohol and water in order to introduce epoxy groups into the gel. 20 ml concentrated aqueous ammonia were added to the resulting epoxy-activated gel and the reaction mixture was stirred for two hours at 50° C. in order to introduce amino groups into the gel.

3 ml of the activated gel thus obtained which contained amino groups were added to 10 ml of an aqueous solution containing 200 mg pentosan polysulphate (pH 4.5). 200 mg 1-ethyl-3-(dimethlaminopropyl)-carbodiimide were added to the resulting reaction mixture, the pH of the reaction mixture being adjusted to 4.5 and the resulting reaction mixture was shaken for 24 hours at 4° C. On completion of the reaction, the resulting reaction mixture was washed in sequence with 2 M aqueous NaCl solution, 0.5 M aqueous NaCl solution and water giving the desired gel on which pentosan polyphosphate was immobilised.

EXAMPLE 2

Prion-containing test samples were treated according to the usual methods with proteinase K to eliminate the normal prion proteins PrPc.

For this purpose, the sample was adjusted to a concentration of 50 μg/ml proteinase K (Boehringer) and incubated for 1 hour at 37° C. Further details regarding the conditions for the enzymatic degradation are described by Schmerr et al, as above.

For example, the following protocol can be used:

50 μl 1 mg/ml proteinase K (Sigma, catalogue no. 82456) are transferred with a pipette into 1 ml of sample.

Incubation at 37° C. is carried out for 30 minutes.

100 μl 4 mM Pefabloc SC PLUS (Roche; catalogue no. 1 873 601) are added. This is followed by incubation for 5 minutes at room temperature.

To the supernatant liquor, beads coated with pentosan polyphosphate from example 1 are added. It has been found that the presence of 1 mM zinc promotes binding.

The beads are sedimented by centrifuging in a Hettich table centrifuge and separated from the test sample.

Subsequently, the beads are incubated with specific antibodies against prions (Prionics AG, University of Zurich, 8057 Zurich, Switzerland) and tested in ELISA by means of a secondary antibody. A positive test batch is characterised by increased addition of the secondary antibody to the ligand complex which in turn can be measured by the conversion of a colourless substrate by the enzyme bound to the second antibody.

It was possible to detect the BSE pathogen in the blood of infected animals in this way in a surprisingly simple manner.

EXAMPLE 3

Instead of an Elisa test, an agglutination test was carried out.

In this way, too, it was possible to detect the BSE pathogen in a surprisingly simple manner.

EXAMPLE 4

Instead of an Elisa test, the beads labelled with the second antibody were detected by means of flow cytometry.

In this way, too, it was possible to detect the BSE pathogen in a surprisingly simple manner.

This procedure for detecting prions is entirely new and practicable. By means of this method, blood samples, tissue samples, body fluids (e.g. urine, milk, liquor, saliva etc.) of animal, human and plant origin can be tested. Soil specimens, too, can be tested for contamination.

EXAMPLE 5

For covalently binding antibodies to nanobeads (FLUO-ROMAX™ fluorescent microparticles, Seradyn, Indianapolis, USA) these are treated with carbodiimide and hydroxysuccinimide in order to ensure a secure and firm binding between the carboxyl groups on the particle surface and the protein molecules (antibodies). In this way, the antibodies remain stably bound to the nanoparticles (longer useful life of the conjugate). The antibodies cannot be separated from the beads during the subsequent treatments (different reaction buffers).

EXAMPLE 6

Detection of the Binding of PrPsc to Pentosan Polyphosphate by Means of Antibody-Europium-Nanobead Complexes.

The europium nanoparticles were purchased from Seradyn, Indianapolis, USA. These particles are "absorbed" with europium chelates in such a way that the surface remains free for coupling reactions and the europium chelates do not escape. Europium chelate: tris(naphthyltrifluorobutanedione) Eu. When these particles are stimulated with UV light (333 nm maximum), they emit light radiation at 613 nm with a duration of approximately 0.5 milliseconds which is 10,000 to 100,000 times longer than the emission period of most flurophores. This extremely long emission period and the large Stokes displacement (difference between emission and excitation wavelength) permit their use in the tests based on time-delayed fluorescence. Each particle contains >30,000 europium atoms in tris-naphthyl trifluorobutanedione (a diketone). For the 100 nm particles, the so-called quantum yield is equivalent to approximately 3,000 molecules of fluorescein (one of the most widely used fluorophores). Phycobiliprotein (probably the most strongly fluorescent known compound), in comparison, has a quantum yield corresponding to that of approximately 30 fluorescein molecules. Since a 100 nm particle has a diameter approximately 10 times bigger than the phycobiliprotein and a 1000 times larger volume mass ratio, these beads have a fluorescence which, on a molar basis, is 100 times higher than that of phycobiliprotein.

The nanoparticles are first irradiated (the so-called excitation wavelength for europium is 340 nm) and, after a delay of 400 μs (in this case), the signals are measured for a length of 400 μs. As a result of this delay, registering non-specific signals of short duration from the matrix is avoided. The results are recorded in RFU (relative fluorescence units). The measuring operation takes place automatically by means of a standardised fluorimeter which can be used to measured time delayed fluorescence.

This system is described by Ci, Y., et al., J. Immun. Meth, 179, 233–241, 1995 as well as Souka et al. Clin. Chem., 47:3, 561–568 among others.

For similar systems (Eu-nanobead conjugates) detection limits for prostate-specific antigens of $7.3 \times 10^5$ molecules/ml are reported (for prion protein, this would correspond to approximately 36.3 fg). The time detection methods previously described are capable of detecting 50 pg prion protein (Barnard, G. et al., Luminescence, 15:6, 357–362, 2000).

EXAMPLE 7

Antibody Coupling to Carriers with the Biotin/Streptavidin System.

Biotin is used in the so-called two step techniques in connection with conjugated or immobilised strept(avidin). The binding of the biotin to the strept(avidin) takes place very rapidly and in a stable manner. Different techniques for the biotinylation of antibodies have been described. Moreover, kits are available from different companies with the corresponding protocol.

Normally, the biotin is conjugated by the primary amines of the proteins (e.g. lysine) and, in this way, 3 to 6 molecules of biotin are bound per protein molecule. As an example, sulpho-NHS-LC-biotin (Pierce) can be used. The separation of the non-conjugated biotin from the antibody can take place by means of NANOSEP™ centrifuge micro-concentrators (Pall). The biotinylation stage is determined photometrically by the so-called HABA reaction (HABA-2-(4'hydroxyazobenzene)-benzoic acid) with excess avidin.

Coating of the nanoparticles with streptavidin is carried out according to Härmä et al, Clin. Chem., 47:3, 561–568 (2001). By prewashing the beads with PBS, pH 7.0 with NANOSEP™ centrifuge microconcentrators, they are resuspended in the same buffer with ultrasonic probe. Subsequently, the activation of the carboxyl groups with 10 mM N-(3-dimethylaminopropyl)-N'-ethylcarbodiimide (EDAC), (Pierce) and N-hydroxysulphosuccinimide (NHS), (Sigma) is carried out for 30 minutes. After two wash processes (as above but with carbonate buffer, pH 9.0), 15 μM streptavidin is added and the beads are incubated for 1 hour. At the end, the nanoparticles are washed 5 times with 2 mM tris-HCl (Sigma), pH 7.0, and stored at 4° C.

EXAMPLE 8

Binding of PrPsc to Europium Nanobeads Via Fibronectin (Compare Example 7).

It has been found in this case that it is particularly important to use a method in the case of which the conformation of the fibronectin molecules is influenced as little as possible.

The separation of the (nano) beads from the sample can take place by centrifuging and/or by using so-called centrifuge concentrators (microfilters). Depending on the strength of the bond between fibronectin and PrPsc, the beads-PrPsc complexes can be washed in order to achieve a maximum possible separation of the two PrP forms.

In principle, the procedure was as follows:
1. Fibronectin is coupled with nanobeads (europium nanobeads)
2. The sample is incubated with fibronectin nanobeads. The pathological form of the PrP (PrPsc) adheres to the fibronectin and the normal form (PrPC) does not—remains dissolved in the reaction mixture.
3. Subsequently, the fibronectin nanobeads are separated from the sample by centrifuging and resuspended in a reaction buffer.
4. The resuspended fibronectin nanobeads are incubated on a microtiter plate coated with monoclonal antibodies (against PrP) (formation of the MoAk-PrPsc-fibronectin-nanobeads complex).
5. After the wash process, the fluorescence is measured (time resolution) and the concentration of PrPsc is determined.

Detailed instructions are as follows:
Human FN (FIBRONECTIN batch: 000832, BD Biosciences. MW: 440 kDa) or other fibronectin recombinants.
1 mg/ml FN: one bottle of 1 mg FN is brought to room temperature and dissolved in 1 ml sterile distilled $H_2O$ for 30 minutes.
0.5 ml 1% MP (Seradyn, FLUORO-MAX fluorescent particles Part no. 1347-0350) is washed 2× with 0.5 ml 50 mM pH 6.1 MES (morpholinoethane sulphonic acid, Sigma product no. M8250) and NANOSEP 300 kDa cut-off (Pall Life Sciences; product no. OD300C33) for 5 minutes at 14,000 G.
After the last wash process, resuspension is carried out in 0.5 ml 50 mM pH 6.1 MES, the suspension is transferred into 2.0 ml Eppendorf tubes and these are filled up to 1.0 ml with 50 mM MES, pH 6.1

Preliminary Activation
a) EDAC (Carbodiimide—Pierce, Cat. No. 22980): 0.6 molar excess, 0.5 ml 1% MP=5 MP; MP acid content meq/g=μmole/mg;
b) (acid content, μmole/mg) (5 mg MP) (desired ratio) =μmole EDAC required: 0.1566×5×0.6=0.4698 μmole EDAC required
c) (μmole EDAC required)/(52 μmole/ml)=ml EDAC stock solution per ml reaction: 0.4698/52=0.009 ml EDAC stock solution
d) EDAC stock solution: 10 mg/ml in distilled water, to be prepared directly before use.
e) Add with a pipette to the washed MP in the following sequence:

230 µl NHS stock solution (50 mg/ml in distilled water N-hydroxysuccinimide, Sigma, cat. No. H7377)
9 µl EDAC stock solution
Incubate for 30 minutes at room temperature with continuous mixing.
Wash MP twice with 50 mM pH 6.1 MES and NANOSEP as in 3.
After the last wash process LWV, resuspend in 0.5 ml 100 mM pH 6.1 MES and transfer into a 2.0 ml Eppendorf tube.
Add 0.5 ml FN solution from 2, mix thoroughly
Incubate for 2 hours at room temperature with continuous mixing
Wash MP twice with 50 mM pH 6.1 MES and NANOSEP as in 3.
After LWV, resuspend in 0.5 ml MNTA (25 mM MOPSO, Sigma cat. No. M8389, pH 7.4; 100 ml mM NaCl, Sigma cat. No. 71378; 0.1% TWEEN 20, Sigma cat. No. 27, 434–8; 0.1% NaN3, Sigma cat. No. 71290)
Store at 4° C.

Coating of the Microtiter Plate
Coat the plate (Nunc, Fluoro-Nunc modules F16 Maxi-Sorp, cat. No. 47515)
6H4 (monoclonal antibody, Prionics): 8 µg/ml, 96 wells—dilute in bic/carb buffer pH 9.4 (Pierce, cat. No. 28382), transfer 50 µl/well with a pipette
Incubate for 3 hours at 37° C.

Blocking of Unspecified Binding Sites
Wash 1×200 µl with wash buffer (5 mM TRIZMA pH 7.8, Sigma cat. No. 93349; 150 mM NaCl; 0.05% Tween20)
Introduce 100 µl blocking buffer (50 mM TRIZMA pH 7.8, Sigma cat. No. 93349; 150 mM NaCl; 2% bovine serum albumine, Immucore cat. No. 004410; 2 gelatine Sigma cat no. G7765; 0.05% TWEEN 20; 0.05% NaN3) with a pipette per cavity.
Shake for 1 hour at room temperature—450 rpm
Suck off supernatant liquor.

Incubation of Antigen MP-FN
Dilute MP-FN 1:742 in PBS-TWEEN 20 2% (PBS Pierce cat. No. 28374; Tween20 2%)
Incubate specimen treated with 50 µl proteinase K in Eppendorf tubes and introduce 50 µl dilute MP-FN with a pipette and incubate for 2 hours at room temperature with continuous mixing
Centrifuge for 2 minutes at 14,000 g with NANOSEP
Discard the filtrate and resuspend MP-FN in 100 µl PBS-TWEEN 20 2%
Place 30 µl per sample accurately into cavity bottom
Incubate for 2 hours at 37° C. at 450 rpm
Wash 2×300 µl PBS-TWEEN 20 2%
Measuring (Time Delayed Fluorescence):
Equipment: Tecan GENios, Program Xfluor4: 10 flashes, delay 400 µs, integration 400 µs.

EXAMPLE 9

Fibronectin is Coupled with Beads (Polystyrene Beads):
Some untreated samples and samples treated with proteinase K are incubated with fibronectin nanobeads
The sample is then incubated with the fibronectin beads.
Subsequently, the fibronectin beads are washed and resuspended in a reaction buffer
The resuspended beads are incubated with a monoclonal fluorescence-labelled antibody (against PrP)
After incubation, the fluorescence signals are measured in a flow cytometre.

EXAMPLE 10

Binding of PrPsc in Microtiter Plates Coated with Fibronectin
1. The microtiter plate is coated with fibronectin
2. The sample is incubated in the microtiter plate. The pathological form of PrP (PrPsc) adheres to the fibronectin and the normal form (PrPc) does not remains dissolved in the reaction mixture.
3. Following the wash process, the europium nanobeads coupled with monoclonal antibody (against PrP) are pipetted into the microtiter plate and incubated.
4. Following the wash process, fluorescence is measured (time resolution) and the concentration of PrPsc determined.

A detailed procedure is as follows, for example:

Coat a Plate (Nunc. Fluoro-Nunc modules F16 Maxi-Sorp. Cat. No. 47515):
Dilute FN 2.5 µg/ml in PBS (Pierce, cat. No. 28374) pH 7.2, introduce 50 µl/well with a pipette
Incubate for 1 hour at room temperature
Remove by suction
Wash plate carefully 3 times with 300 µl distilled water.

Antigen Incubation:
Introduce sample treated with 30 µl proteinase K with a pipette into the cavities
Incubate for 1.5 hours at room temperature—450 rpm MP-3F4 Incubation:
Wash once with 200 µl PBS-TWEEN 20 2%
Dilute MP 1:296 in PBS-TWEEN 20 2%
Thoroughly mix the dilution
Pipette 30 µl accurately onto cavity bottom
Incubate for 4 hours at 30° C. —shake at 450 rpm
Wash twice with 200 µl PBS Tween20 2%

Measuring:
Equipment: Tecan GENios, program XFluor4: 10 flashes, delay 400 µs, integration 400 µs.

EXAMPLE 11

Binding of PrPsc to Europium Nanoparticles Via Lipoprotein A.
For procedure compare Example 9 (instead of fibronectin, lipoprotein A was used. Apolipoprotein A can also be used).

EXAMPLE 12

Binding of PrPsc to Polystyrene Beads Coated with Lipoprotein A.
For procedure compare example 10 (instead of fibronectin, lipoprotein A was used. Apolipoprotein A can also be used).

EXAMPLE 13

Binding of PrPsc in Microtiter Plates Coated with Lipoprotein A.
For procedure compare example 11 (instead of fibronectin, lipoprotein A was used. Apolipoprotein A can also be used).

The invention claimed is:
1. An in vitro process for detecting bovine spongiform encephalopathy (BSE) pathogens (PrPsc) in a sample, comprising the steps of

(a) treating the sample with proteinase K to degrade non-pathogenic prion proteins in the sample;

(b) contacting the sample thus treated with a first PrPsc-binding principle which is bound to a solid carrier whereby pathogenic PrPsc in the sample is bound to said first PrPsc-binding principle;
(c) separating the first binding principle bound to the solid carrier from the sample; and
(d) detecting any pathogenic PrPsc bound to the first binding principle, the first binding principle being selected from the group consisting of glycosaminoglycans, fibronectin, lipoprotein A, and Congo red.

2. Process according to claim 1, comprising detecting the pathogenic PrPsc in step (d) with a PrPsc-specific monoclonal antibody.

3. Process according to claim 1, wherein the solid carrier is labeled for detection to provide a labeled carrier, the method comprising separating the labeled carrier from the sample in step (c) by binding to a second binding principle comprising an antibody specific for PrPsc, and detecting the label.

4. Process according to claim 1, wherein the first binding principle is a glycosaminoglycan selected from the group consisting of heparan sulphate, heparin, hyaluronic acid, chondroitin sulphate, dermatan sulphate, and keraton sulphate.

5. Process according to claim 1, wherein the first binding principle is an artificially produced sulphonated glycosaminoglycan.

6. Process according to claim 1, wherein the sample originates from a human or animal body.

7. Process according to claim 1, wherein the sample is a blood sample, tissue sample, or a body fluid.

8. Process according to claim 1, wherein the sample is thrombic material subjected to lysis.

9. Process according to claim 1, wherein the solid carrier is a microcarrier (bead).

10. Process according to claim 2, comprising detecting the pathogenic PrPsc with a PrPsc-specific monoclonal antibody coupled to a nanobead with a diameter of 10 nm–100 nm which contains europium and wherein the process further comprises the step of detecting the pathogenic PrPsc by means of time-delayed fluorescence.

11. Process according to claim 1 comprising detecting the pathogenic PrPsc bound to the first binding principle in step (d) by time-delayed fluorescence of nanobeads containing europium bound to the first binding principle.

12. Process according to claim 1 comprising using microtiter plates as solid carrier.

13. Process according to claim 1 comprising using a sintered glass filter as solid carrier.

14. A diagnostic system kit for detecting bovine spongiform encephalopathy (BSE) pathogens (PrPsc) in a sample, said kit comprising proteinase K for treating a sample, a PrPsc-binding principle for contacting the protenaise K treated sample, said binding principle being bound to a solid carrier, and a detection system comprising a PrPsc-specific antibody for detecting pathogenic PrPsc being bound to the PrPsc-binding principle, said binding principle being selected from the group consisting of glycosaminoglycans, fibronectin, lipoprotein A, and Congo red.

15. Process according to claim 7, wherein the sample is a body fluid selected from the group consisting of urine, milk, liquor, and saliva.

16. Kit according to claim 14, additionally comprising a second antibody directed against said PrPsc-specific antibody.

* * * * *